(12) United States Patent
Hasson et al.

(10) Patent No.: US 9,061,278 B2
(45) Date of Patent: Jun. 23, 2015

(54) MICROFLUIDIC SYSTEMS AND METHODS FOR THERMAL CONTROL

(75) Inventors: Kenton C. Hasson, Germantown, MD (US); Johnathan S. Coursey, Germantown, MD (US); Gregory H. Owen, Clarksburg, MD (US); Hiroshi Inoue, Bethesda, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 765 days.

(21) Appl. No.: 12/825,476

(22) Filed: Jun. 29, 2010

(65) Prior Publication Data

US 2011/0048547 A1     Mar. 3, 2011

Related U.S. Application Data

(60) Provisional application No. 61/221,452, filed on Jun. 29, 2009.

(51) Int. Cl.
| | |
|---|---|
| *G01K 7/16* | (2006.01) |
| *G01N 7/00* | (2006.01) |
| *B01L 3/00* | (2006.01) |
| *B01L 7/00* | (2006.01) |
| *H05B 1/02* | (2006.01) |

(52) U.S. Cl.
CPC ........... *B01L 3/502715* (2013.01); *B01L 7/525* (2013.01); *B01L 2200/147* (2013.01); *B01L 2300/1805* (2013.01); *H05B 1/02* (2013.01)

(58) Field of Classification Search
None
See application file for complete search history.

(56) References Cited

U.S. PATENT DOCUMENTS

| | | | |
|---|---|---|---|
| 3,882,725 A | 5/1975 | Rao et al. | |
| 4,218,916 A | * 8/1980 | Mutziger | ...................... 374/170 |
| 5,445,635 A | 8/1995 | Denen et al. | |

(Continued)

FOREIGN PATENT DOCUMENTS

| | | |
|---|---|---|
| JP | 2002-297108 A | 10/2002 |
| JP | 2005-99821 A | 4/2005 |

(Continued)

OTHER PUBLICATIONS

Liu, Chung N., Nicholas M. Toriello, and Richard A. Mathies. "Multichannel PCR-CE microdevice for genetic analysis." Analytical chemistry 78.15 (2006): 5474-5479.*

(Continued)

*Primary Examiner* — In Suk Bullock
*Assistant Examiner* — Robert Eom
(74) *Attorney, Agent, or Firm* — Rothwell, Figg, Ernst & Manbeck, P.C.

(57) ABSTRACT

The invention relates to methods and devices for control of an integrated thin-film device with a plurality of microfluidic channels. In one embodiment, a microfluidic device is provided that includes a microfluidic chip having a plurality of microfluidic channels and a plurality of multiplexed resistive thermal detectors (RTDs). Each of the RTDs is associated with one of the microfluidic channels. The RTDs are connected to a power supply through individual electrodes and pairs of common electrodes. Adjacent RTDs may be driven with alternating polarities, and the current in the common electrodes may be minimized using a virtual ground circuit. The compact microfluidic device is capable of fast heating and highly precise thermal control. The compact microfluidic device is also capable using the RTDs to sense temperature without their heating capability.

16 Claims, 15 Drawing Sheets

(56) References Cited

U.S. PATENT DOCUMENTS

| | | | |
|---|---|---|---|
| 5,767,259 A * | 6/1998 | Albagli et al. | 536/23.1 |
| 6,356,191 B1 * | 3/2002 | Kirkpatrick et al. | 340/501 |
| 6,612,737 B1 | 9/2003 | Lobban | |
| 6,622,746 B2 | 9/2003 | Yang et al. | |
| 6,852,287 B2 * | 2/2005 | Ganesan | 422/502 |
| 6,960,437 B2 | 11/2005 | Enzelberger et al. | |
| 7,394,182 B2 | 7/2008 | Pelrine et al. | |
| 7,440,684 B2 | 10/2008 | Spaid et al. | |
| 2002/0140662 A1 | 10/2002 | Igarashi | |
| 2005/0019902 A1 | 1/2005 | Mathies et al. | |
| 2005/0042639 A1 | 2/2005 | Knapp et al. | |
| 2005/0052274 A1 | 3/2005 | Mattoon et al. | |
| 2007/0241068 A1 | 10/2007 | Pamula et al. | |
| 2009/0060795 A1 | 3/2009 | Owen et al. | |
| 2009/0061489 A1 | 3/2009 | Hanagata et al. | |

FOREIGN PATENT DOCUMENTS

| | | |
|---|---|---|
| JP | 2009-15334 A | 1/2009 |
| WO | 2005075683 A1 | 8/2005 |
| WO | 2007/092643 A2 | 8/2007 |
| WO | 2009/032087 A1 | 3/2009 |

OTHER PUBLICATIONS

Luo, Ching-Hsing, et al. "A Portable Polymerase Chain Reaction Device by MEMS and Neural Network Technologies." Asia-Pacific Conference of Transducerss and Micro-Nano Technology, Sapporo, Japan. 2004.*
Shadpour, Hamed, et al. "Multichannel microchip electrophoresis device fabricated in polycarbonate with an integrated contact conductivity sensor array." Analytical chemistry 79.3 (2007): 870-878.*
Kelly et al., "Microfluidic Systems for Integrated, High-Throughput DNA Analysis," Analytical Chemistry, (2005) pp. 96-102.
Kopp et al., "Chemical Amplification: Continuous-Flow PCR on a Chip," Science, vol. 280, (1998) pp. 1046-1048.
Lagally et al., "Single-Molecule DNA Amplification and Analysis in an Integrated Microfluidic Device," Analytical Chemistry, vol. 73, No. 3, (2001) pp. 565-570.
Park et al., "Cylindrical compact thermal-cycling device for continuous-flow polymerase chain reaction," Analytical Chemistry, vol. 75 (2003) pp. 6029-6033.

* cited by examiner

MICROFLUIDIC SYSTEMS AND METHODS FOR THERMAL CONTROL

CROSS REFERENCE TO RELATED APPLICATION

This application claims the benefit of Provisional Patent Application Ser. No. 61/221,452, filed Jun. 29, 2009, the contents of which are incorporated herein by reference in their entirety.

BACKGROUND

1. Field of Invention

The present invention relates to microfluidic devices and temperature control of the microfluidic devices for performing biological reactions. More specifically, the present invention relates to systems and methods for determining and controlling the temperature of integrated resistive heater elements in microfluidic devices.

2. Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, identification of crime scene features, the ability to propagate industrial organisms and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. Polymerase chain reaction (PCR) is a well-known technique for amplifying deoxyribonucleic acid (DNA). With PCR, one can produce millions of copies of DNA starting from a single template DNA molecule. PCR includes phases of "denaturation," "annealing," and "extension." These phases are part of a cycle which is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

The PCR process phases of denaturing, annealing, and extension occur at different temperatures and cause target DNA molecule samples to replicate themselves. Temperature cycling (thermocyling) requirements vary with particular nucleic acid samples and assays. In the denaturing phase, a double stranded DNA (dsDNA) is thermally separated into single stranded DNA (ssDNA). During the annealing phase, primers are attached to the single stranded DNA molecules. Single stranded DNA molecules grow to double stranded DNA again in the extension phase through specific bindings between nucleotides in the PCR solution and the single stranded DNA. Typical temperatures are 95° C. for denaturing, 55° C. for annealing, and 72° C. for extension. The temperature is held at each phase for a certain amount of time which may be a fraction of a second up to a few tens of seconds. The DNA is doubled at each cycle, and it generally takes 20 to 40 cycles to produce enough DNA for certain applications. To have good yield of target product, one has to accurately control the sample temperatures at the different phases to a specified degree.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Many detection methods require a determined large number of copies (millions, for example) of the original DNA molecule, in order for the DNA to be characterized. Because the total number of cycles is fixed with respect to the number of desired copies, the only way to reduce the process time is to reduce the length of a cycle. Thus, the total process time may be significantly reduced by rapidly heating and cooling samples to process phase temperatures while accurately maintaining those temperatures for the process phase duration.

Accordingly, there is a need in the art for a compact microfluidic device capable of fast heating and highly precise thermal control.

SUMMARY

The present invention relates to systems and methods capable of fast heating and highly precise thermal control of microfluidic devices. In some embodiments, this is accomplished by systems and methods for precisely determining and controlling the temperature of integrated thin film resistive thermal detectors in a microfluidic device. The present invention also relates to systems and methods capable high quality temperature measurements of microfluidic devices.

In one aspect, the present invention provides a microfluidic system having a microfluidic device and a heater control and measurement circuit. In one embodiment, the microfluidic device includes: a plurality of microchannels, a plurality of resistive temperature detectors (RTDs) each adjacent to a portion of an associated one of the plurality of microchannels, a first common electrode connected to each of the plurality of RTDs, and a second common electrode connected the first common electrode and to each of the plurality of RTDs. In one embodiment, the heater control and measurement circuit is configured to: (i) drive the plurality of RTDs with heater control signals having alternating polarities so that adjacent RTDs of the plurality are driven with heater control signals having opposite polarities, (ii) minimize the current in the first and second common electrodes, (iii) sense a temperature of each of the plurality of RTDs, and (iv) update the heater control signals using the sensed temperatures of the plurality of RTDs.

In some embodiments, the portions of the associated ones of the plurality of microchannels are located in a polymerase chain reaction (PCR) thermal zone of the microfluidic device or in a thermal melt zone of the microfluidic device. Also, the heater control and measurement circuit may include a system controller that is configured to generate the heater control signals based on a polymerase chain reaction (PCR) profile or a temperature ramp profile.

In some embodiments, the microfluidic device further includes: a second plurality of RTDs, a third common electrode connected to each of the second plurality of RTDs, and a fourth common electrode connected the third common electrode and to each of the second plurality of RTDs; and the heater control and measurement circuit is further configured to: (i) drive the second plurality of RTDs with heater control signals having alternating polarities so that adjacent RTDs of the second plurality of RTDs are driven with heater control signals having opposite polarities; (ii) minimize the current in the third and fourth common electrodes; (iii) sense a temperature of each of the second plurality of RTDs; and (iv) update the heater control signals using the sensed temperatures of the second plurality of RTDs.

In some embodiments, the heater control and measurement circuit is configured to update the heater control signals by modulating the amplitude of the heater control signals. The heater control signals may be alternating current signals, and the heater control signals may have opposite polarities when they are 180 degrees out of phase with each other.

In another aspect, the present invention provides a method for individually controlling a plurality of resistive thermal detectors (RTDs) of a microfluidic device of a microfluidic system, wherein the RTDs are each adjacent to a portion of an associated one of the plurality of microchannels. The method includes the steps of: generating heater control signals having alternating polarities to drive the plurality of RTDs, supplying the heater control signals to the plurality of RTDs so that adjacent RTDs of the plurality of RTDs are driven with heater control signals having opposite polarities, minimizing current in first and second common electrodes, wherein the first and second common electrodes are each connected to each RTD of the plurality of RTDs, sensing a temperature of each of the plurality of RTDs, and updating the heater control signals using the sensed temperatures of the plurality of RTDs. The heater control signals may be generated and updated based on a polymerase chain reaction (PCR) profile or on a temperature ramp profile. The minimizing the current in the first and second common electrodes may include determining a current imbalance between currents of the heating control signals supplied to the plurality of RTDs. Also, the minimizing the current in the first and second common electrodes may include sourcing/sinking the determined current imbalance. The method may also include preventing the heater control signals from having a voltage lower than a minimum voltage limit.

In some embodiments, the microfluidic device includes a second plurality of RTDs, and the method further includes: generating second heater control signals having alternating polarities to drive the second plurality of RTDs; supplying the second heater control signals to the second plurality of RTDs so that adjacent RTDs of the second plurality of RTDs are driven with second heater control signals having opposite polarities; minimizing current in third and fourth common electrodes, wherein the third and fourth common electrodes are each connected to each RTD of the second plurality of RTDs; sensing a temperature of each of the second plurality of RTDs; and updating the second heater control signals using the sensed temperatures of the second plurality of RTDs.

Each of the second plurality of RTDs may be adjacent to a second portion of an associated one of the plurality of microchannels. The heater control signals that drive the plurality of RTDs may be generated so that deoxyribonucleic acid (DNA) contained in the associated ones of the plurality of microchannels is amplified. The second heater control signals that drive the second plurality of RTDs may be generated so as to ramp the temperature of the second plurality of RTDs. The DNA amplification may be achieved through a polymerase chain reaction (PCR).

The microfluidic device may include a second plurality of microchannels. Each of the second plurality of RTDs may be adjacent to a portion of an associated one of the second plurality of microchannels. The first and second heater control signals that respectively drive the first and second plurality of RTDs may be generated so that deoxyribonucleic acid (DNA) contained in the portions of the associated ones of the plurality of microchannels and the second plurality of microchannels is amplified. The DNA amplification is achieved through a polymerase chain reaction (PCR).

The microfluidic device may include a second plurality of microchannels, each of the second plurality of RTDs being adjacent to a portion of an associated one of the second plurality of microchannels, and the first and second heater control signals that respectively drive the first and second plurality of RTDs are generated to ramp the temperature of the first and second plurality of RTDs.

In some embodiments, the heater control signals are updated by modulating the amplitude of the heater control signals. The heater control signals may be alternating current signals, the heater control signals have opposite polarities when they are 180 degrees out of phase with each other.

In another aspect, the present invention provides a microfluidic system including a microfluidic device and a heater control and measurement circuit. The microfluidic device may include a first microchannel; a second microchannel; a first electrode; a second electrode; a first common electrode; a second common electrode; a first resistive temperature detector (RTD) adjacent to a portion of the first microchannel and connected to the first electrode and to the first and second common electrodes; a second RTD adjacent to a portion of the second microchannel and connected to the second electrode and to the first and second common electrodes. The heater control and measurement circuit may include: a virtual ground circuit associated with the first and second common electrodes and configured to minimize the current in the first and second common electrodes, a first RTD control circuit and a second RTD control circuit. The virtual ground circuit may have: (i) an input connected to the first common electrode, and (ii) an output connected to the second common electrode. The first RTD control circuit may have: (i) an input connected to the first common electrode, and (ii) an RTD control output connected to the first electrode. The second RTD control circuit may have: (i) an input connected to the first common electrode, and (ii) an RTD control output connected to the second electrode. The heater control and measurement circuit is configured such that the first and second RTDs are driven with opposite polarities.

In another aspect, the present invention provides a method for individually controlling first and second resistive thermal detectors (RTDs) of a microfluidic device of a microfluidic system, wherein the first RTD is adjacent to a portion of a first microchannel of the microfluidic device, and the second RTD is adjacent to a portion of a second microchannel of the microfluidic device. The method includes: generating a first heater control signal for driving the first RTD and a second heater control signal for driving the second RTD; supplying the first heater control signal to the first RTD using a first electrode connected to the first RTD; supplying the second heater control signal to the second RTD using a second electrode connected to the second RTD; minimizing current in first and second common electrodes, wherein the first and second common electrodes are each connected to the first and second RTDs; and sensing a temperature of the first RTD and a temperature of the second RTD using a signal received from the first common electrode. The first and second RTDs may be driven with opposite polarities.

In another aspect, the present invention provides a microfluidic system including a microfluidic device and an RTD measurement circuit. The microfluidic device may include: a plurality of microchannels; a plurality of resistive temperature detectors (RTDs) each adjacent to a portion of an associated one of the plurality of microchannels; a first common electrode connected to each of the plurality of RTDs; and a second common electrode connected the first common electrode and to each of the plurality of RTDs. The RTD measurement circuit may be configured to: (i) invert a drive signal into an inverted drive signal; (ii) drive every other RTD of the plurality of RTDs with the drive signal; (iii) drive the RTDs of the plurality of RTDs that are not driven with drive signal with the inverted drive signal; (iv) minimize the current in the first and second common electrodes; and (v) sense a temperature of each of the plurality of RTDs.

In another aspect, the present invention provides a method for sensing the temperature of a plurality of resistive thermal detectors (RTDs) of a microfluidic device of a microfluidic system, wherein the RTDs are each adjacent to a portion of an associated one of the plurality of microchannels. The method may include: generating a drive signal; inverting the drive signal into an inverted drive signal; driving every other RTD of the plurality of RTDs with the drive signal; driving the RTDs of the plurality of RTDs that are not driven with drive signal with the inverted drive signal; minimizing current in first and second common electrodes, wherein the first and second common electrodes are each connected to each RTD of the plurality of RTDs; and sensing a temperature of each of the plurality of RTDs.

In another aspect, the present invention provides a microfluidic system including a microfluidic device and a heater control and measurement circuit. The microfluidic device may include: a plurality of microchannels; a plurality of resistive temperature detectors (RTDs) each adjacent to a portion of an associated one of the plurality of microchannels; and a common electrode connected to each of the plurality of RTDs. The heater control and measurement circuit may be configured to: (i) drive the plurality of RTDs with heater control signals having alternating polarities so that adjacent RTDs of the plurality are driven with heater control signals having opposite polarities; (ii) sense a temperature of each of the plurality of RTDs; and (iii) update the heater control signals by modulating the amplitude of the heater control signals in accordance with the sensed temperatures of the plurality of RTDs.

In another aspect, the present invention provides a method for individually controlling a plurality of resistive thermal detectors (RTDs) of a microfluidic device of a microfluidic system, wherein the RTDs are each adjacent to a portion of an associated one of the plurality of microchannels. The method may include: generating heater control signals having alternating polarities to drive the plurality of RTDs; supplying the heater control signals to the plurality of RTDs so that adjacent RTDs of the plurality of RTDs are driven with heater control signals having opposite polarities; sensing a temperature of each of the plurality of RTDs; and updating the heater control signals by modulating the amplitude of the heater control signals in accordance with the sensed temperatures of the plurality of RTDs.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF PREFERRED EMBODIMENTS

Embodiments of the systems and methods for determining and controlling the temperature of integrated resistive thermal detectors in a microfluidic device are described herein with reference to the figures.

Figure 1:
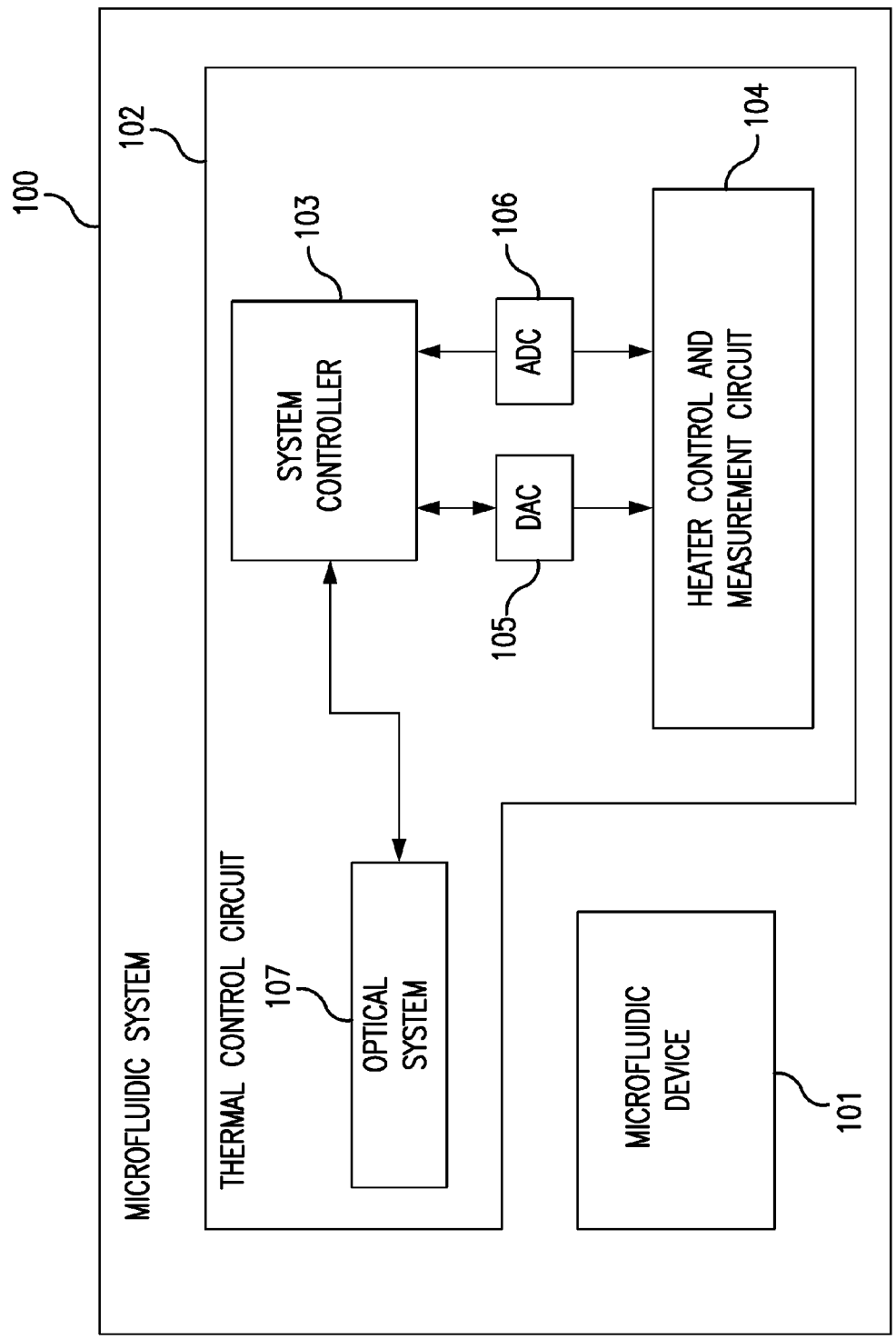
FIG. 1 depicts a block diagram illustrating functional units of a microfluidic system according to one embodiment.

FIG. 1 illustrates a microfluidic system 100 according to one embodiment of the present invention. As shown in FIG. 1, microfluidic system 100 has a microfluidic device 101 and a thermal control circuit 102. Thermal control circuit 102 has a system controller 103, heater control and measurement circuit 104, digital to analog converter (DAC) 105 and analog to digital converter (ADC) 106. Although DAC 105 and ADC 106 are shown in FIG. 1 as separate from system controller 103 and heater control and measurement circuit 104, DAC 105 and ADC 106 may alternatively be part of system controller 103 or heater control and measurement circuit 104. In addition, thermal control circuit 102 may include an optical system 107 to monitor microfluidic device 101.

Figure 2:
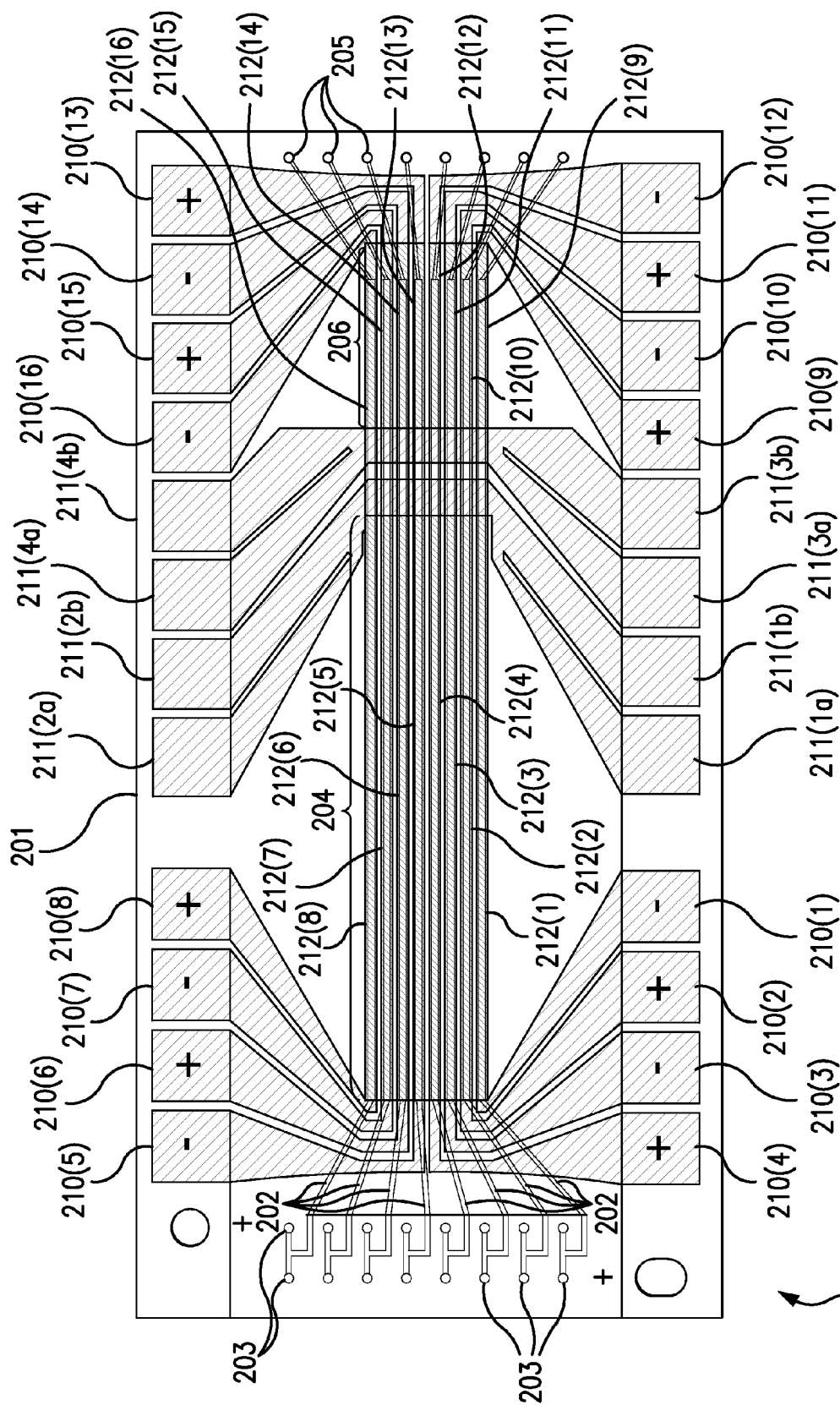
FIG. 2 depicts a top view of a microfluidic device of the microfluidic system according to one embodiment.

Compact microfluidic devices require numerous functions within a limited space. In one embodiment, the present invention is a highly efficient microfluidic device 101 for use in molecular diagnostics. Two possible specific applications are polymerase chain reaction (PCR) and high resolution thermal melt. The microfluidic device 101 shown in FIG. 2 illustrated a plurality of microchannels 202 that are adjacent to thin-film resistive temperature detectors (RTDs) 212, in accordance with one embodiment. For example, in one non-limiting embodiment, microchannels 202 may be underlain with RTDs 212. The RTDs 212 function as precise temperature sensors as well as quick response heaters. Further, to decrease waste heat and better thermally isolate separate functional zones 204 and 206, the thin-film RTDs include lead wires or electrodes 210 and 211 which are more conductive than the RTDs 212. The electrodes 210 and 211 may be any suitable conductive material and, in one preferred embodiment, are gold. The RTDs 212 may be made from any suitable resistive material that demonstrates good response to temperature and is capable of being used as a heater. Suitable RTD materials include, but are not limited to, platinum and nickel.

PCR is one of the most common and critical processes in molecular diagnostics and other genomics applications that require DNA amplification. In PCR, target DNA molecules are replicated through a three phase temperature cycle of denaturation, annealing, and extension. In the denaturation step, double stranded DNA is thermally separated into single stranded DNA. In the annealing step, primers hybridize to single stranded DNA. In the extension step, the primers are extended on the target DNA molecule with the incorporation of nucleotides by a polymerase enzyme.

Typical PCR temperatures are 95° C. for denaturation, 55° C. for annealing, and 72° C. for extension. The temperature during a step may be held for an amount of time from fractions of a second to several seconds. In principle, the DNA doubles in amount at each cycle, and it takes approximately 20 to 40 cycles to complete a desired amount of amplification. To have good yield of target product, one has to control the sample temperatures at each step to the desired temperature for each step. To reduce the process time, one has to heat and cool the samples to desired temperature very quickly, and keep those temperatures for the desired length of time to complete the synthesis of the DNA molecules in each cycle. This can be accomplished, in accordance with one embodiment, using microfluidic chip 101 with thin-film RTDs 212 as heaters.

As shown in FIG. 2, microfluidic device 101 may have a plurality of microfluidic channels 202 extending across a substrate 201. The illustrated embodiment shows eight channels 202; however, fewer or more channels could be included. Each channel 202 may include one or more inlet ports 203 (the illustrated embodiment shows two inlet ports 203 per channel 202) and one or more outlet ports 205 (the illustrated embodiment shows one outlet port 205 per channel 202). Each channel may include a first portion extending through a PCR thermal zone 204 and a second portion extending through a thermal melt zone 206. A sipper (not illustrated) can be used to draw liquid into the plurality of microfluidic channels 202.

The microfluidic device 200 further includes heater elements, which may be in the form of thin film resistive thermal detectors (RTDs) 212. In one embodiment, one or more heater element 212 are associated with each microfluidic channel 202 and are located adjacent to the microfluidic channel 202. For example, each microfluidic channel 202 may be situated above (or otherwise adjacent to) on one or more heating element 212. In the illustrated embodiment, heater element 212(1)-(8) are associated with the microfluidic channels 202 in PCR thermal zone 204 and heater elements 212(9)-(16) are associated with the microfluidic channels located in thermal melt zone 206. For example, in the non-limiting illustrated embodiment, heater elements 212(1) and 212(9) are associated with one microfluidic channel 202 with heater element 212(1) being located in PCR thermal zone 204 and heater element 212(9) being located in thermal melt zone 206.

In one embodiment, heater electrodes 210 and 211 provide electrical power to the plurality of heating elements 212. To best utilize the limited space provided by substrate 201 of microfluidic device 101 and reduce the number of electrical connections required, multiple RTDs share a pair of common electrodes 211. Heater electrodes 210 and 211 include individual electrodes 210 and common electrodes 211. Each pair of common electrodes includes, for example, a first common electrode 211(*a*) and a second common electrode 211(*b*). The pairs of common electrodes 211 allow the microfluidic sensors to be controlled in three-wire mode.

Figure 3:
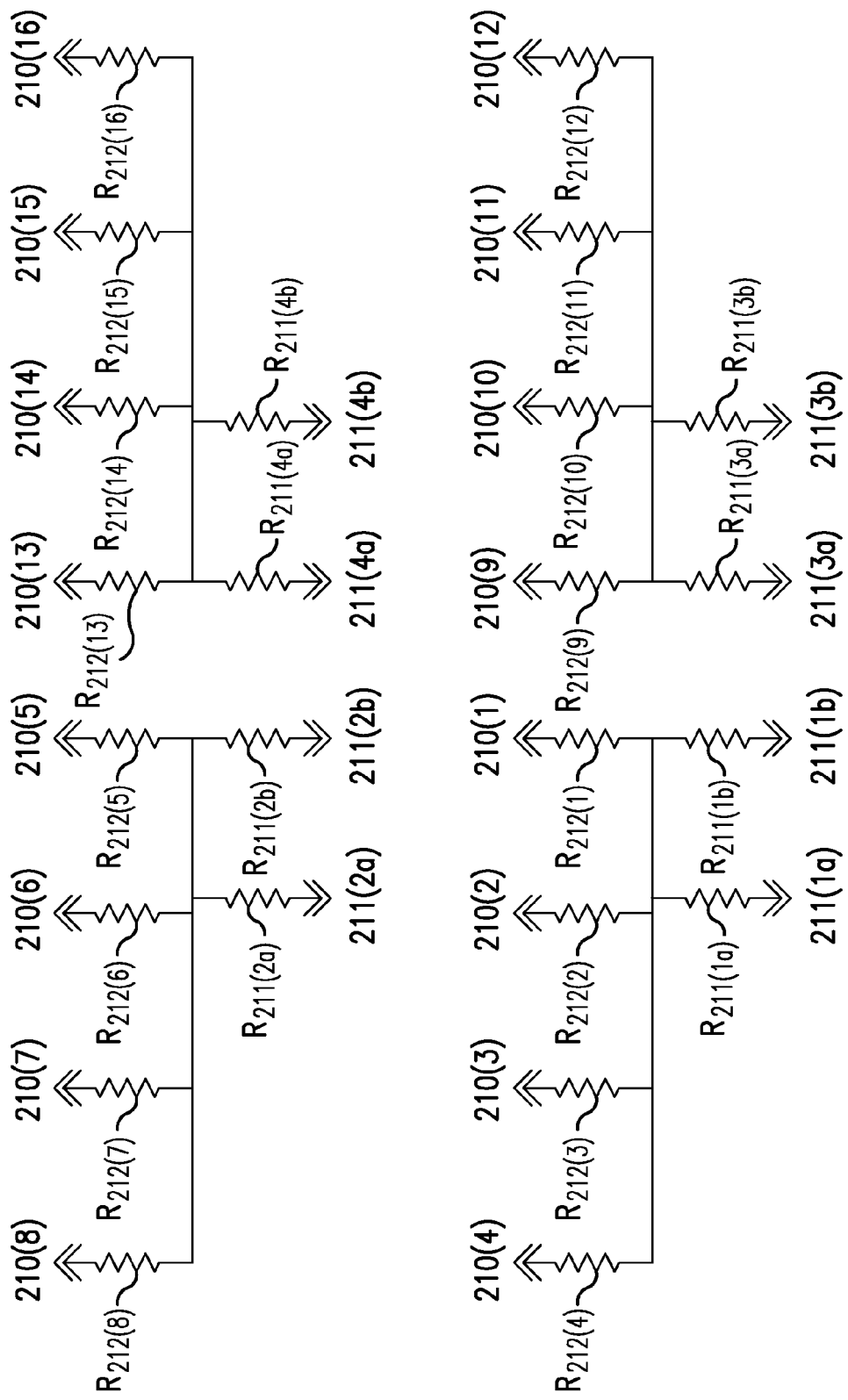
FIG. 3 depicts a resistive network for multiplexed thermal detectors of the microfluidic device of FIG. 2 according to one embodiment.

In the non-limiting illustrated embodiment, there are sixteen RTD heater elements 212(1)-212(16), sixteen individual electrodes 210(1)-210(16) and four common electrode pairs 211(1)-211(4). Accordingly, as illustrated in FIG. 2, there are four first common electrodes 211(1*a*)-211(4*a*) and four second common electrodes 211(1*b*)-211(4*b*). Each heater element 212 is connected to an individual electrode 210 and a pair of common electrodes 211. Multiple heater elements 212 share a pair of common electrodes 211 and are thereby multiplexed with the pair of common electrodes 211. For example, RTD 212(1) is connected to individual electrode 210(1) and a pair of common electrodes 211(1*a*) and 211(1*b*). FIG. 3 illustrates the thin-film resistance network associated with the RTDs 212 and electrodes 210 and 211 of the microfluidic device 101 shown in FIG. 2, in accordance with one embodiment.

Although the microfluidic device 101 and resistor network shown in FIGS. 2 and 3 has four heater elements 212 connected to each of the four pairs of common electrodes 211, more or fewer RTDs may be multiplexed with each pair of common electrodes 211. Furthermore, more or fewer pairs of common electrodes 211 may be used to create more or fewer multiplexed sets of heater elements.

In one embodiment, each of the heater elements 212 of microfluidic device 101 is independently controlled for rapid heating and temperature sensing. As a result, the temperature of a microfluidic channel 202 in PCR thermal zone 204 may be controlled independently of the temperature of the microfluidic channel 202 in thermal melt zone 206. Also, the temperature of each microfluidic channel 202 in a zone 204 or 206 may be controlled independently of the temperature of the other microfluidic channels 202 in the zone 204 or 206.

Figure 4:
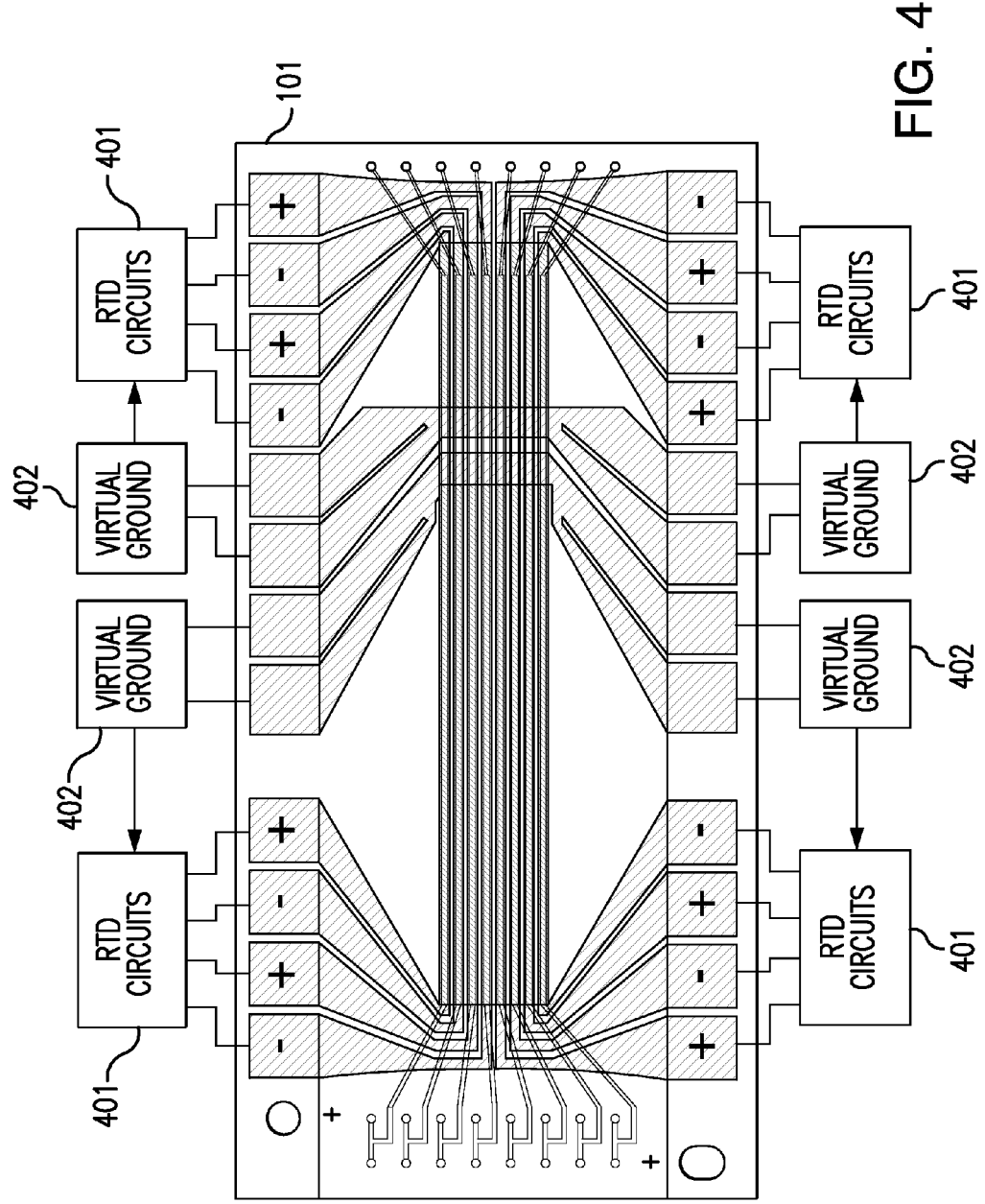
FIG. 4 depicts a block diagram illustrating functional units of a heater control and measurement circuit and their connections with electrodes of the microfluidic device of FIG. 2 according to one embodiment.
Figure 5:
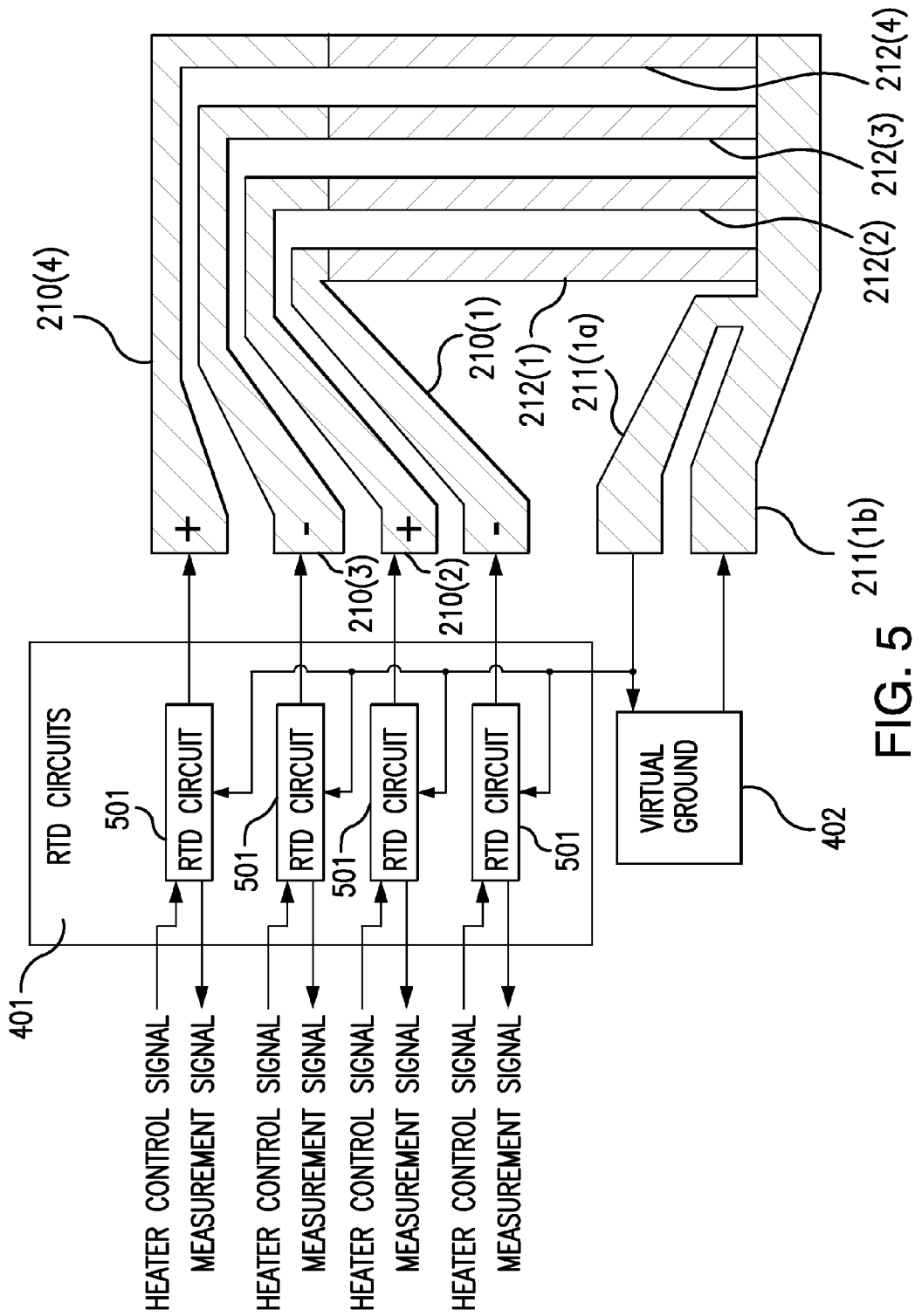
FIG. 5 depicts a block diagram illustrating further detail of the functional units of the heater control and measurement circuit of FIG. 4 and their connections with electrodes of the microfluidic device of FIG. 2 according to one embodiment.
Figure 6:
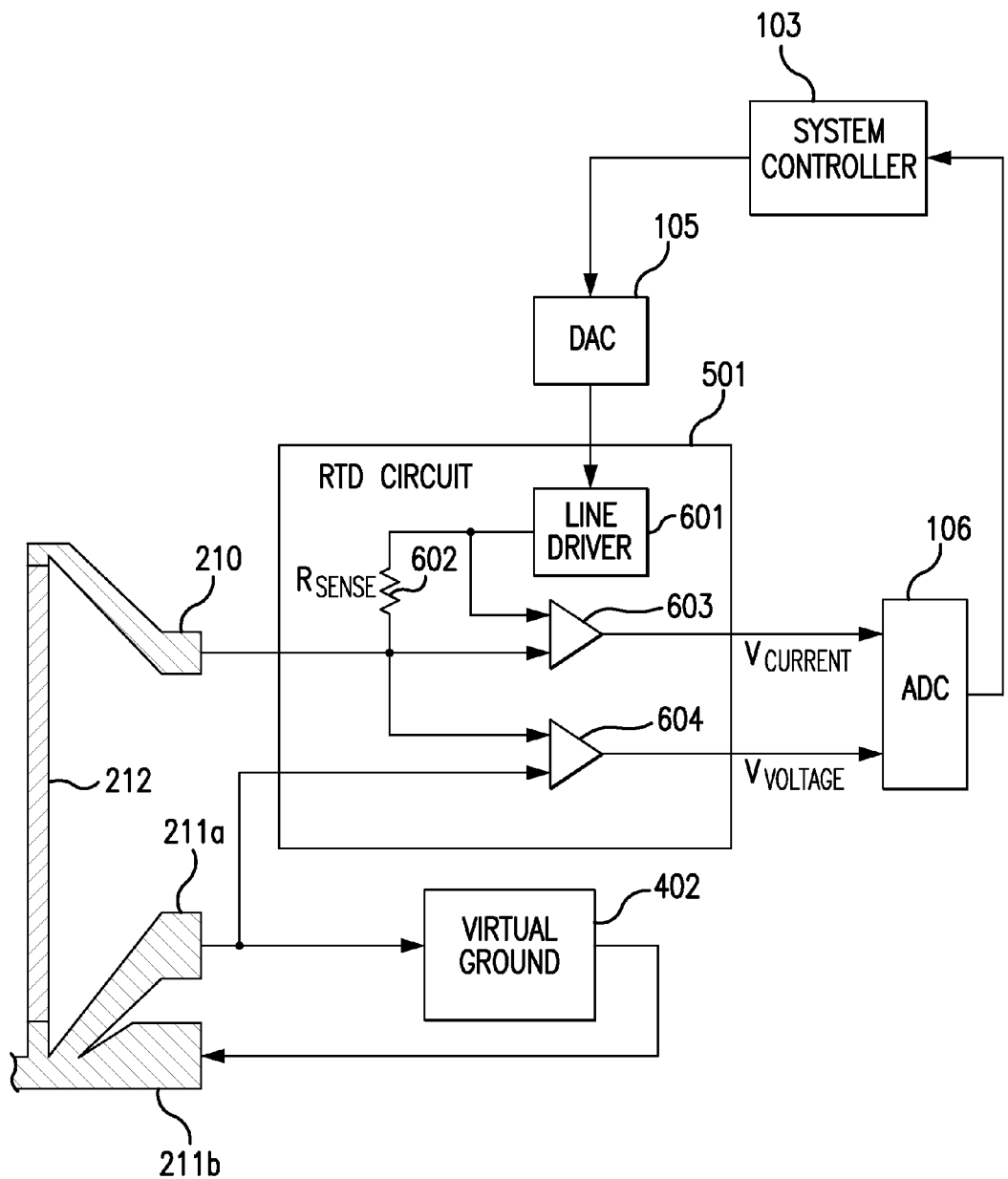
FIG. 6 depicts a schematic diagram illustrating a thermal control circuit for a single resistive thermal detector according to one embodiment.

FIGS. 4-6 illustrate the configuration of heater control and measurement circuit 104 according to one embodiment. FIG. 4 shows the general configuration of heater control and measurement circuit 104 and, generally, the manner in which heater control and measurement circuit 104 is connected to the heater electrodes 210 of microfluidic device 101. The heater control and measurement circuit 104 may include groups of RTD control circuits 401 and virtual ground circuits 402, as shown in FIG. 4. Each group of RTD control circuits 401 is associated with a set of multiplexed RTDs 212. Each virtual ground circuit 402 is associated with one of pair of common electrodes 211.

FIG. 5 shows the configuration of a group of RTD control circuits 401 and shows the manner in which one group of RTD control circuits 401 and one virtual ground circuit 402 are connected to the electrodes 210 of a set of multiplexed RTDs 212, in accordance with one embodiment. Specifically, the connections to individual electrodes 210(1)-210(4), first common electrode 211(1a) and second common electrode 211(1b) are shown to provide an illustrative example. Heater control and measurement circuit 104 may be connected to the individual electrodes 210 and common electrodes 211 associated with the other sets of multiplexed RTDs 212 in a similar fashion.

As shown in FIG. 5, a group of RTD circuits 401 includes a plurality of RTD circuits 501. Each RTD circuit 501 is associated with one RTD 212 (e.g., 212(1)) and has an RTD control output connected to the individual electrode 210 (e.g., 210(1)) that is connected to the associated RTD 212. Further, each RTD circuit 501 has an input connected to the first common electrode 211 (e.g., 211(1a)) of the common electrode pair (e.g., 211(1)) connected to the associated RTD 212. The temperature of each RTD 212 is individually controlled and measured by its own RTD circuit 501.

FIG. 6 schematically illustrates the configuration of an RTD circuit 501 used for thermal control of a single thin-film RTD 212, in accordance with one embodiment. The manner in which RTD circuit 501 is connected with the individual electrode 210, first common electrode 211a and second common electrode 211b associated with an RTD 212 are also shown.

As shown in FIG. 6, each RTD circuit 501 comprises a line driver circuit 601, sense resistor 602, and differential amplifiers 603 and 604. Each RTD circuit 501 receives a heater control signal from system controller 103 through DAC 105. Line driver circuit 601 may be either a non-inverting line driver circuit 601 or an inverting line driver circuit 601. Sense resistor 602 is connected in series with RTD 212, and differential amplifier 603 is configured to measure the voltage drop Vcurrent across the sense resistor 602. Because sense resistor 602 is connected in series with an RTD 212, the voltage drop across the sense resistor 602 is indicative of the current across the RTD 212. Differential amplifier 604 is configured to measure the voltage drop Vvoltage across RTD 212. The signals Vcurrent and Vvoltage respectively output from differential amplifiers 603 and 604 are transmitted to system controller 103 through ADC 106.

As stated above, each virtual ground circuit 402 is associated with a pair of common electrodes 211. As shown in FIGS. 5 and 6, according to an embodiment, a virtual ground circuit 402 has an input connected to a first common electrode 211a of the associated pair of common electrodes 211 and an output connected a second common electrode 211b of the associated pair of common electrodes 211.

Figure 7:
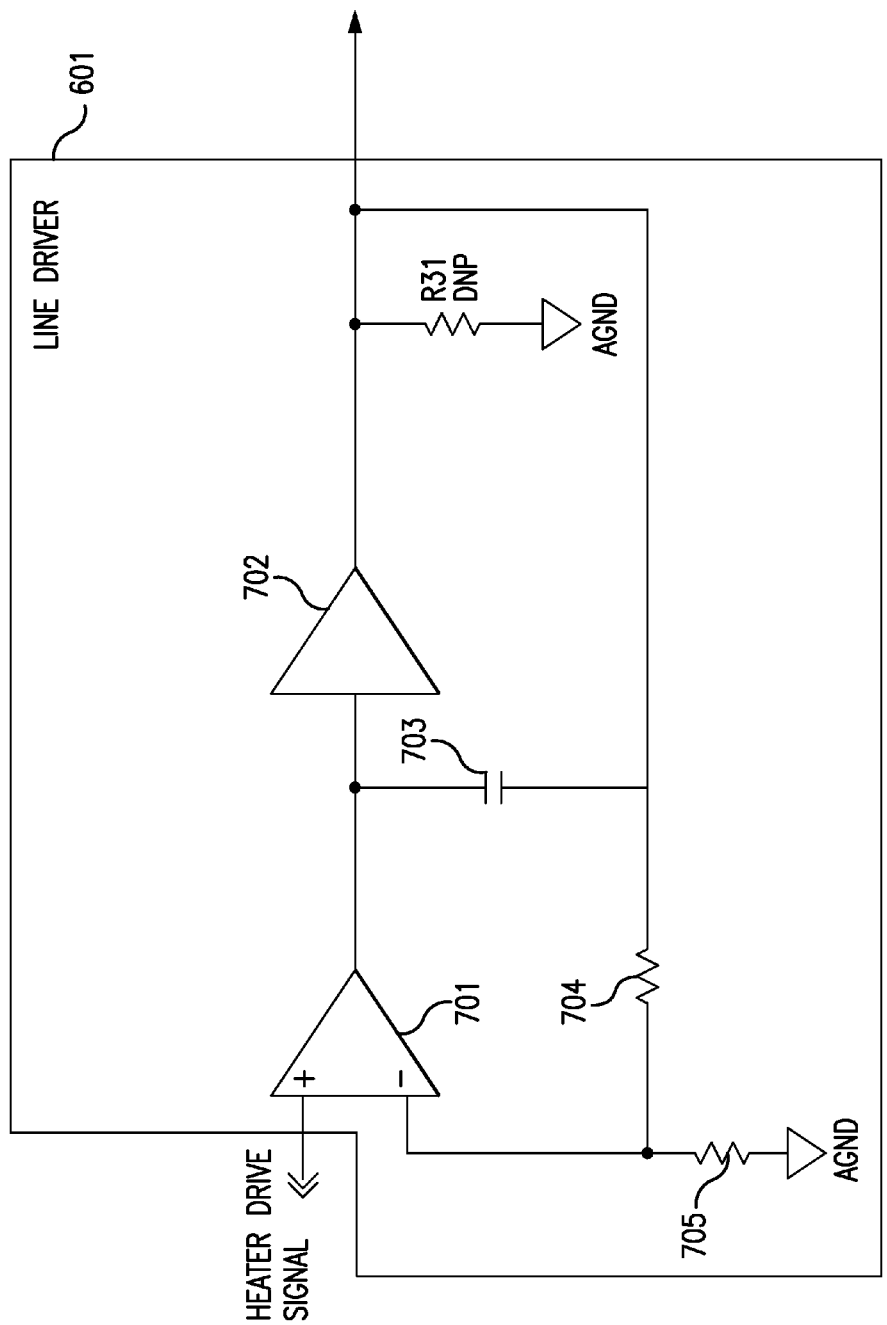
FIG. 7 depicts a schematic diagram illustrating a line driver according to one embodiment.

FIG. 7 illustrates the configuration of a non-inverting line driver 601 according to one embodiment. Line driver circuit 601 comprises an operational amplifier 701 followed by a power buffer 702. Line driver circuit 601 additionally comprises capacitor 703 and resistors 704 and 705.

Figure 8:
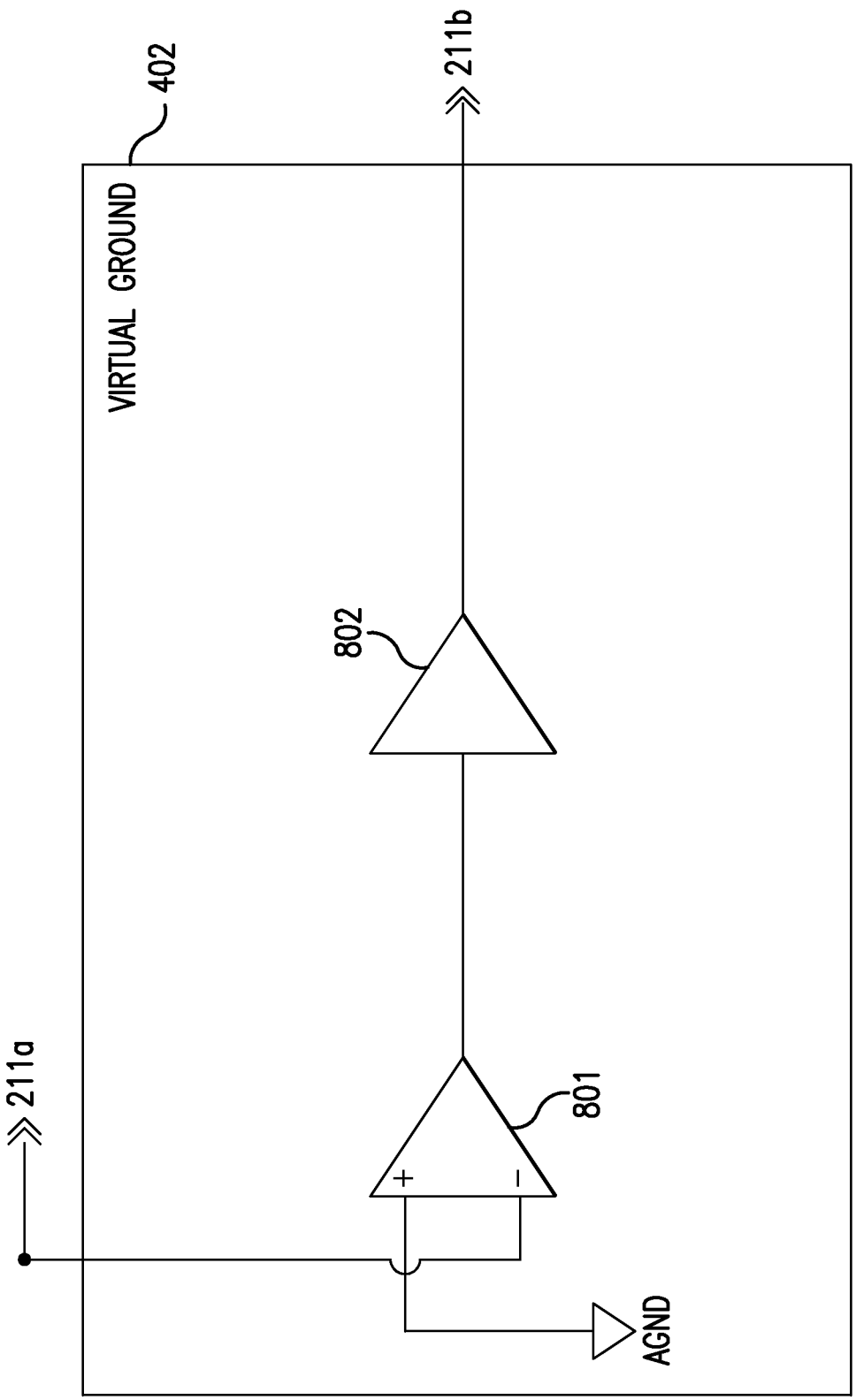
FIG. 8 depicts a schematic diagram illustrating a virtual ground circuit according to one embodiment.

FIG. 8 illustrates the configuration of a virtual ground circuit 402 according to one embodiment. Virtual ground circuit 402 comprises an operational amplifier 801 followed by a power buffer 802. Operational amplifier 801 has a first input connected to a first common electrode 211a and a second input connected to ground. The output of operational amplifier 801 is input into power buffer 802. The output of power buffer 802 is connected to a second common electrode 211b.

Figure 11:
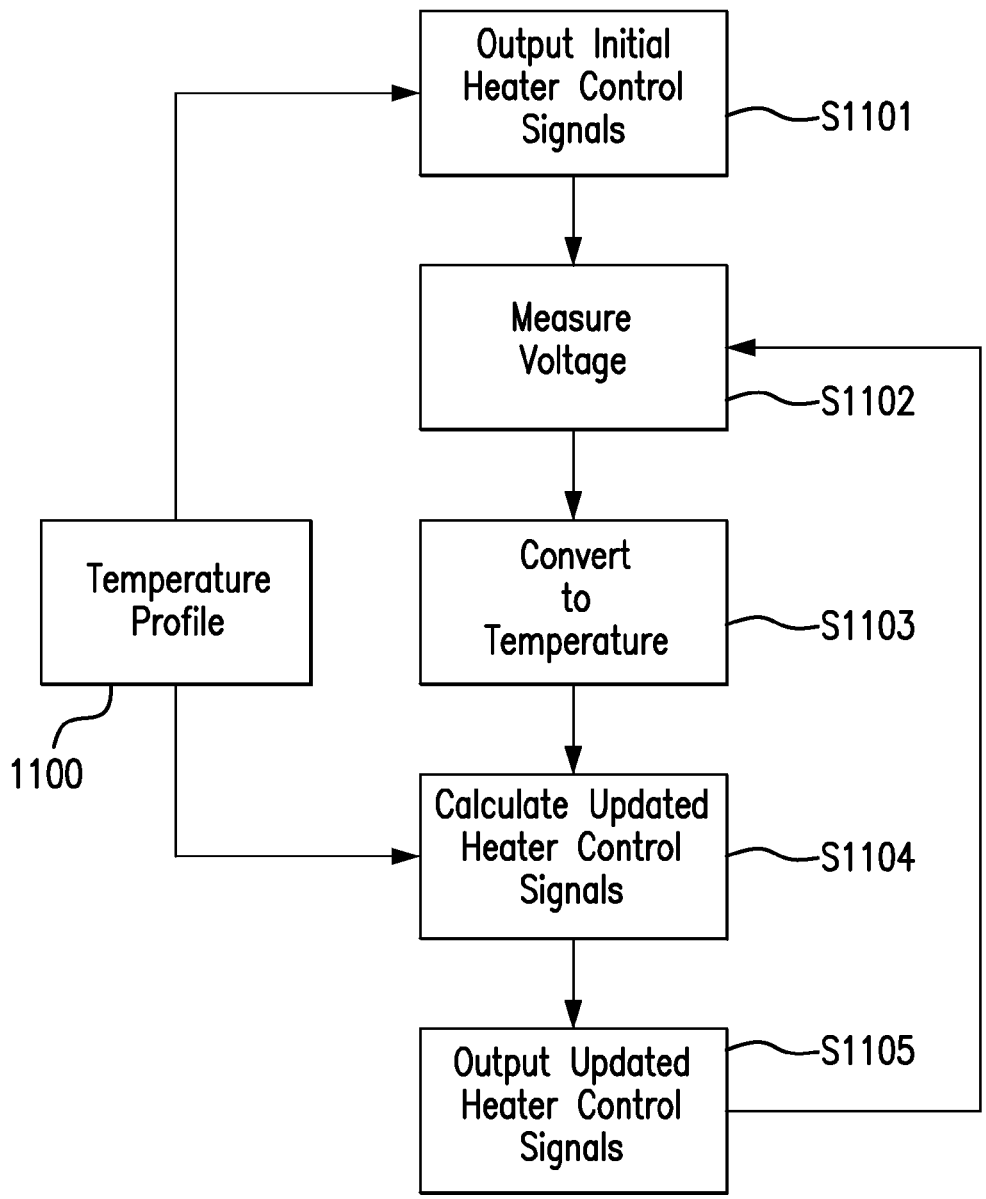
FIG. 11 depicts a flow chart showing a closed-loop thermal control algorithm according to one embodiment.

In operation, the thin-film RTDs 212 may be used for temperature sensing as well as rapid heating. System controller 103 may utilize both of these functions to perform high speed closed-loop thermal control of RTDs 212. A flow chart illustrating the closed-loop thermal control according to one embodiment in shown in FIG. 11. At step S1101, system controller 103 outputs initial heater control signals to the RTD circuits 501 of heater control and measurement circuit 104 through DAC 105. System controller 103 may use temperature setpoints output from one or more temperature profiles 1100 to generate the heater control signals. For example, system controller 103 may have a PCR profile for generating heater control signals for RTDs 212 located in PCR thermal zone 204 of microfluidic device 101 and a thermal ramp profile for generating heater control signals for RTDs 212 located in thermal melt zone 206 of microfluidic device 101.

The temperature of each of the RTDs 212 is sensed. Temperature sensing may be achieved by performing steps S1102 and S1103. In step S1102, the currents and voltage drops across each of the RTDs 212 are measured. The currents across each of the RTDs 212 may be measured by using the differential amplifiers 603 of the RTD circuits 501 to detect the voltage drops Vcurrent across the sense resistors 602 connected in series with the RTDs 212. The voltage drops Vvoltage across each of the RTDs 212 may be measured by using the differential amplifiers 604 of the RTD circuits 501 having inputs respectively connected to the individual electrode 210 and first common electrode 211 to which the RTD 212 is connected. In step S1103, the measured currents and voltage drops are converted to temperatures, which may be accomplished using the two-step process shown in FIG. 12.

Figure 12:
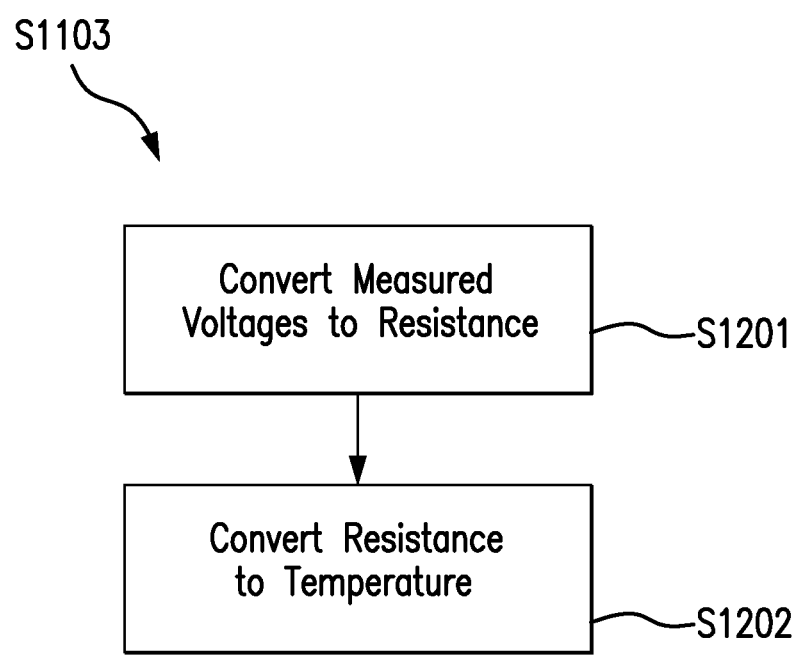
FIG. 12 depicts a flow chart showing a measured voltage to temperature conversion algorithm according to one embodiment.

As shown in FIG. 12, the conversion to temperature may involve steps S1201 and S1202. In step S1201, the resistance of each RTD 212 is determined using the ratio of the measured currents to the measured voltages (i.e., Vvoltage/Vcurrent). In step S1202, the determined resistances of the RTDs 212 are converted to the temperatures of the RTDs 212. The conversion of resistance to temperature may be achieved using a simple mathematic expression or lookup table. Given an RTD 212 with sufficient linearity over the temperatures of interest, one may determine the resistance with just two calibration coefficients (i.e., Temperature=k0+(k1*Resistance)). The specific expression used to determine temperature may be altered by the system designers to give the appropriate level of accuracy for a particular application. Specifically, for example, a quadratic relationship may be appropriate for some materials and applications.

After the temperature of the RTDs 212 has been sensed, in step S1104, system controller 203 calculates updated heater control signals. The updated heater control signals may be calculated using temperature setpoints from one or more temperature profiles 1100, such as the PCR profile and thermal ramp profile described above. In addition, the updated heater control signals may be calculated using proportional-integral-derivative (PID) control (i.e., three-term control). Under PID control, the weighted sum of proportional, integral and derivative values may be used to adjust/update the heater control signals where the proportional value determines the reaction to the current error, the integral value determines the reaction based on the sum of recent errors, and the derivative value determines the reaction based on the rate at which the error has been changing.

In step S1105, the system controller 103 outputs the updated heater control signals to the RTD circuits 501 of heater control and measurement circuit 104 through DAC 105. The process then begins again at step S1102.

The heater driving performed by thermal control circuit 102 of the microfluidic system 100 will now be described. Heating of the thin-film heater/sensor RTDs 212 may be digitally controlled and, in a preferred embodiment, is amplitude modulated. Amplitude modulation is preferred because a continuous modest change in voltage, rather than large voltage steps, avoids slew rate limits and improves settling time. However, since the heater control is digital, various heating schemes are possible and easily implemented. For example, pulse width modulation (PWM) and alternating current (AC) concepts may also be used.

In some embodiments, to heat heater elements 212, system controller 103 outputs a heater control signal that instructs a DAC 105 to output a suitable voltage, whose magnitude is determined by the thermal load. Suitable DACs include multifunction data acquisition (DAQ) devices such as the PXI-6289 from National Instruments, as well as numerous other analog output cards available. Some of the desired characteristics of the DAC include the resolution, absolute accuracy, linearity, response time, and current output capabilities. Specifically, the DAC should have sufficient bit resolution to ensure the desired precision of heating. With too low a resolution for the heater drive signal, the RTD 212 will oscillate around the desired set point. A multifunction DAQ device should address these characteristics as well as have sufficient number of output channels to provide independent control of the multiplexed RTDs 212. Alternatively, system controller 103 could be configured to output digital signals through a digital output device which are interpreted by an integrated circuit that features many DACs 105, such as, for example, the LTC2600 Octal 16-bit rail-to-rail DACs from Linear Technology.

Many otherwise suitable DACs lack sufficient current sourcing capabilities for the desired heating. One specific application where this is of concern is in PCR. The throughput of a PCR platform can be dramatically increased if PCR cycle times are reduced. Having excess heating capability (large current sourcing) can reduce the denature and extension transition times. Furthermore, it allows the system to overcome highly efficient cooling means which are desired for fast annealing but would reduce the heating rate. To improve the current sourcing capabilities, in accordance with one embodiment, a power buffer circuit (i.e., line driver circuit) 601 pre-conditions the DAC signal before it is used by an RTD circuit 501. One such line driver 601 is the combination power buffer 702 with operational amplifier 701 circuit shown in FIG. 7. Operational amplifier 701 may be, for example, Linear Technology Operational Amplifier LT1012. Power buffer 702 may be, for example, Linear Technology Power Buffer LT1010. The desired characteristics of this circuit 601 are the response time, current output capacity, noise, linearity, operating voltage, and absolute accuracy. In a preferred embodiment, power buffer 702 is capable of providing up to 150 mA of current.

It may also be desirable to amplify or attenuate the DAC's signal with the above described line driver circuit 601. For example, with fast PCR it may be desirable to drive the thin-film RTDs 212 with up to 20 V for fast heating. A typical DAC 105 may have insufficient range to achieve this voltage (such as is the case with the PXI-6289 which can output up to plus/minus 10V). In some embodiments (preferred for PCR), the line driver circuit 601 could be configured to provide 2 times gain to the original DAC output. This amplification could be realized with inverting or non-inverting feedback (see FIG. 7) since the DAC 105 is capable of bi-polar output.

In another example, with a smaller thermal load it may be desirable to drive the thin-film RTDs with less than the full range of the DAC 105. In this case, it would be desirable to attenuate the DAC signal before it reaches the thin-film RTD 212. Attenuation allows the entire range of the DAC to be used while driving the load with a lower voltage (resulting in improved resolution of the driving signal and a smoother temperature with less oscillation). The line driver circuit 601 could be used to attenuate the DAC signal by adding a voltage divider between the DAC and the power buffer, or alternatively, the line driver circuit 601 could feature inverting feedback with gain less than 1. A line driver circuit 601 with inverting feedback that attenuates the DAC signal by a factor of 2 is preferred for high resolution thermal melt. Specifically, the preferred embodiments for PCR and thermal melt both include inverting feedback in the line driver circuits 601, which reduces the complexity of the combined system. Further, it may be desirable for the amplification and attenuation circuits to include programmable resistances such as digital potentiometers or DACs that could alter the gain/attenuation at the direction of the system controller 103. The variable gain/attenuation circuits may be useful for a system and sensor controller that operate on different types of microfluidic devices 101 or are required to run different thermal protocols.

Further, in accordance with one preferred embodiment, the thermal control circuit 102 is configured for bi-polar driving potential. This can be achieved through digital control of bi-polar DACs 105, or alternatively, the output of uni-polar DACs 105 could be inverted with the circuitry of line driver circuit 601. The bi-polar driving potential or alternating polarity of the heater driving signals functions in concert with the virtual grounding circuits 402, which are described in further detail below.

In FIGS. 2, 4 and 5, the individual electrodes 210 have been labeled with pluses (+) and minuses (−) to illustrate the alternating polarity of the heater drive signals with which the RTDs 212 may be driven, in accordance with one embodiment. Individual electrodes 210 driven with heater driving signals having a positive polarity are not structurally different from individual electrodes 210 driven with heater driving signals having a negative polarity. The pluses (+) and minuses (−) with which the individual electrodes 210 have been labeled merely provide an illustrative example of the bi-polar driving of RTDs 212. Further, the specific manner with which RTDs 212 have been labeled in FIGS. 2, 4 and 5 is not limiting. For example, RTDs 212(1)-212(8) and/or RTDs 212(9)-212(16) could be driven with polarities opposite than the polarities shown in FIG. 2. Alternating the polarities of the heater drive signals in combination with the virtual grounding of the common electrodes 211 reduces the current density in and temperature of the common electrodes 211 compared to uni-polar driving in which all RTDs are driven with heater driving signals have the same polarity.

The virtual ground circuit 402 shown in FIG. 8, in accordance with one embodiment, works in conjunction with the alternating polarity of the heater driving signals to reduce the current in the pairs of common electrodes 211. Minimizing the current in the pairs of common electrodes 211 decreases waste heat, which is advantageous from a system level and improves the thermal isolation of microfluidic functional zones 204 and 206 in which, for example, PCR and high resolution thermal melt are performed. Furthermore, decreasing the unwanted heating of the common electrodes 211 improves the specificity of the temperature measurement because, for example, at least one of the common electrodes 211 must be used for temperature measurement.

In accordance with embodiments, the function of the virtual ground circuit 402 is to utilize a pair of common electrodes 211 to drive those common electrodes to near zero potential. Further, in some embodiments, nearly all of the current in the pair of common electrodes 211 is contained in one of the common electrodes 211 (e.g., second common electrode 211b), leaving the other common electrode 211 (e.g., first common electrode 211a) available for temperature sensing as will be described in further detail below.

In one embodiment, a virtual grounding circuit 402 is implemented for each pair of common electrodes 211 (i.e., one virtual ground circuit 402 for each multiplexed set of RTDs 212). As described above, the number of RTDs sharing a pair of common electrodes 211 may be chosen for the specific application. However, in some embodiments, it is desirable to consider the current imbalance that may result. If all of the multiplexed RTDs 212 were driven with the same polarity potential, then a large current would flow through one of the common leads 211 (e.g., second common electrode 211b). In contrast, with bi-polar driving signals, any current imbalance will be much smaller. Specifically, positive driving signals tend to cancel out negative ones. A small current imbalance may still exist due to imperfections in the thin-film RTDs 212, differences in RTD layout, or non-uniformity of cooling. In some embodiments, the preferred condition would be a symmetric layout in which polarities alternated for each RTD (e.g., positive/negative/positive/negative). If true symmetry were achieved, there would be no current imbalance and nearly no current in the common electrodes 211.

Further, in some embodiments, the virtual grounding circuit 402 may be capable of sourcing/sinking a resulting current imbalance. In an embodiment, operational amplifier 801 may be, for example, Linear Technology Operational Amplifier LT1012, and power buffer 802 may be, for example, Linear Technology Power Buffer LT1010. In one preferred embodiment, the power buffer 802 is capable of providing up to 150 mA of current.

Figure 13:
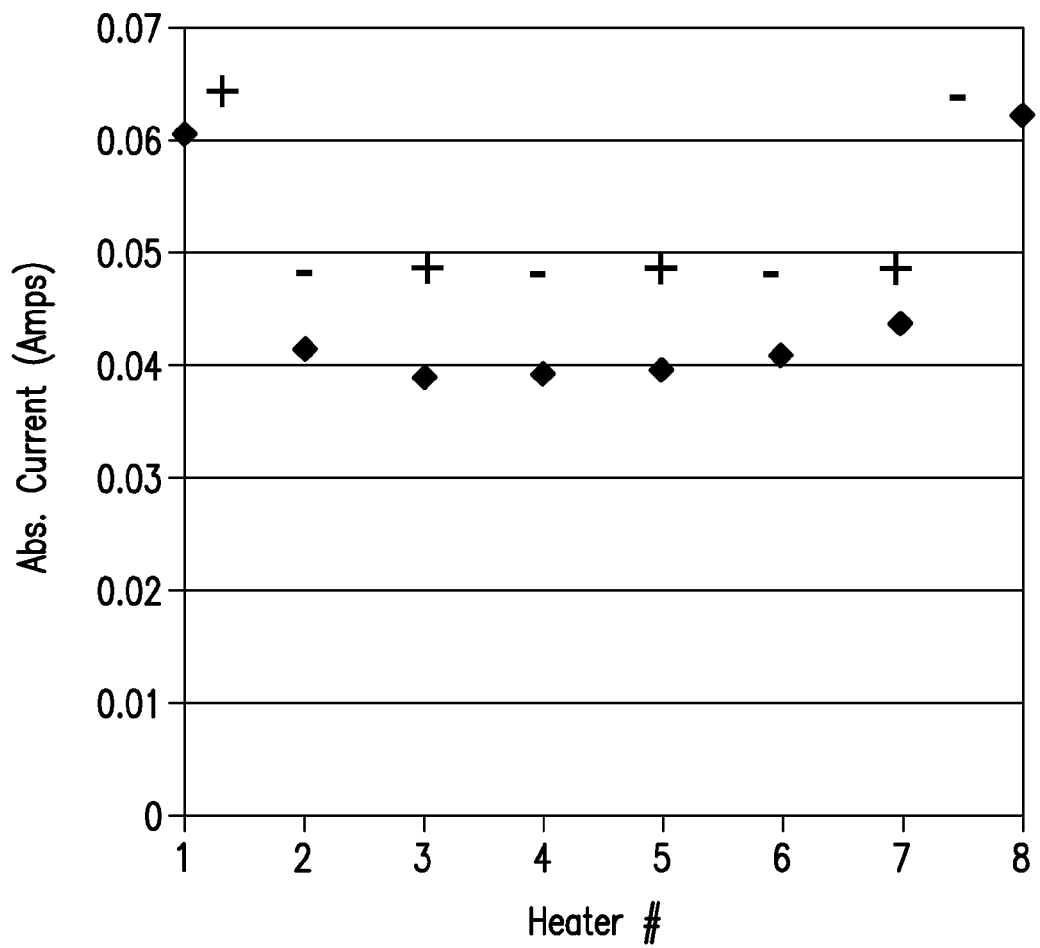
FIG. 13 shows an example of a small current imbalance resulting from driving eight of the heaters shown in FIG. 2 to 70° C. with alternating polarity combined with the non-uniform thermal load that must be sourced/sinked by the virtual ground circuit.

The following non-limiting example describes how a small current imbalance may result in a pair of common electrodes 211 in the microfluidic system 100 shown in FIG. 1 and how this current imbalance may be offset. In the example, heater driving signals having an alternating polarity were used to drive RTDs 212(1)-212(8) of the microfluidic device 101 shown in FIG. 2. Positive drive voltages were used with odd RTDs 212 (e.g., 212(1), 212(3), 212(5) and 212(7)) and negative voltages were used with even RTDs 212 (e.g., 212(2), 212(4), 212(6) and 212(8)). RTDs 212(1)-212(8) were each heated to 70° C. Due to the symmetric nature of the device, the absolute currents required to heat each RTD 212 to 70° C. exhibited a symmetric profile, as shown in FIG. 13. Because outside RTDs 212(1) and 212(8) heat the boundaries, outside RTDs 212(1) and 212(8) may require significantly more power than RTDs 212(2)-212(7). As RTDs 212(1)-212(4) share a pair of common electrodes 211(1a) and 211(1b), a small current imbalance is preferably sourced/sinked by the virtual ground circuit 402 associated with common electrodes 211(1a) and 211(1b). In this case, the virtual ground circuit 402 associated with common electrodes 211(1a) and 211(1b) supplies about −20 mA. Similarly, as RTDs 212(5)-212(8) share a pair of common electrodes 211(2a) and 211(2b), a small current imbalance is preferably sourced/sinked by the virtual ground circuit 402 associated with common electrodes 211(2a) and 211(2b). In this case, the virtual ground circuit 402 associated with common electrodes 211(2a) and 211(2b) supplies about +20 mA.

To sense the temperature of the RTDs 212, each RTD 212 is measured individually by measuring the current and voltage drop across the RTD 212. The current is measured using a precise sense resistor 602 that is placed in series with the RTD 212, as is shown in FIG. 6. An example of a suitable sense resistor 602 is the LVS3 0.5 ohm 15 ppm wire wound surface mount resistor from Precision Resistor Co., Inc. Alternatively, and preferably, the sense resistor 602 may be a film resistor such as Y16070R50000F9W from Vishay Precision Group. Desired characteristics of the current sense resistor 602 are high precision and low temperature coefficient of resistance. In preferred embodiments, care should be taken in the layout of the heater control and measurement circuit 104 to ensure that the sense resistor 602 is in a consistent thermal environment and free from electro-magnetic interference. Furthermore, the resistance of the sense resistor 602 should be large enough to provide a suitable signal but not too large as to decrease the ability of the circuit to rapidly heat the RTDs 212. As such, it is preferable to condition the current sense signal.

To improve the signal to noise ratio (SNR), the differential amplifier 603 that determines the voltage drop Vcurrent across the current sense resistor 602 may be an instrumentation amplifier, such as, for example, the LT1167 from Linear Technologies. Characteristics of a preferred embodiment of the differential amplifier 603 include its accuracy, response time, and operating voltage limits. The differential amplifier 603 may include gain to improve SNR. Specifically, the gain should be sufficient to utilize the entire range of the ADCs 106, which is typically a range such as −10 to 10 Volts. It may be preferable for the gain of the differential amplifier 603 to be programmable by using a digital potentiometer or DAC for the gain resistor. The system controller 103 could then program the variable gain resistor to improve the SNR. Some applications of this include a system and sensor controller 103 that can operate different types of microfluidic devices 101 that feature different resistances or are used at different temperatures or in different thermal environments. Alternatively, the ADC 106 could be chosen to include variable range such as with the PXI-6289 multifunction DAQ, which can operate at ranges as small as plus/minus 1 V and as high as plus/minus 10 V. In this configuration, the range of the ADC 106 would be set as required by the application.

A measure of the voltage drop Vvoltage across the RTD 212 is also required to determine the RTD resistance. The differential amplifier 604 that determines the voltage drop Vvoltage across the RTD 212 may be an instrumentation amplifier, such as the LT1167 from Linear Technologies. Because the common electode 211 that is connected to the input of the virtual ground circuit 402 passes little to no current, it is preferable to measure the RTD voltage drop Vvoltage as referenced to this common electode 211. As shown in FIGS. 5 and 6, the first common electrode 211a is the common electrode 211 connected to the input of the virtual ground circuit 402.

In one embodiment, the system controller 103 is configured to have a minimum voltage limit for the heater/sensor driving signal. Specifically, it is desirable for the output of DAC 105 to be maintained at least a minimum DAC output. If the DAC output were allowed to go to zero (or below some pre-determined threshold), in some embodiments, there would be no voltage or current to sense and the system controller 103 would be blind to the true temperature of the RTDs 212. Care should be taken to ensure that the minimum voltage limit is not too high, as this could prevent the RTD from cooling rapidly. Furthermore, if the minimum voltage limit is sufficiently high, the RTDs 212 may not cool to a low desired temperature. In some embodiments, a minimum voltage limit of 400 mV may be appropriate, but the limit may vary based on circuit components, desired accuracy, and thermal profile required.

Cabling connecting the RTDs to the heating control and measurement circuit 104 of the thermal control circuit 102 may be designed to reduce any corruption of the precise temperature measurement signal. Preferably, the cabling is low resistance, protected from electro-magnetic noise (shielded, twisted, etc.), and thermally stable (including having a low temperature coefficient of resistance). Furthermore, it may be preferred that the sensor cable be wired for 4-wire resistance measurement to mitigate adverse cable effects such as the sensitivity of the cable resistance to temperature. Since the common electrodes 211 are already paired, only 1 additional wire is required for each sensor to yield 4-wire measurements.

Figure 9:
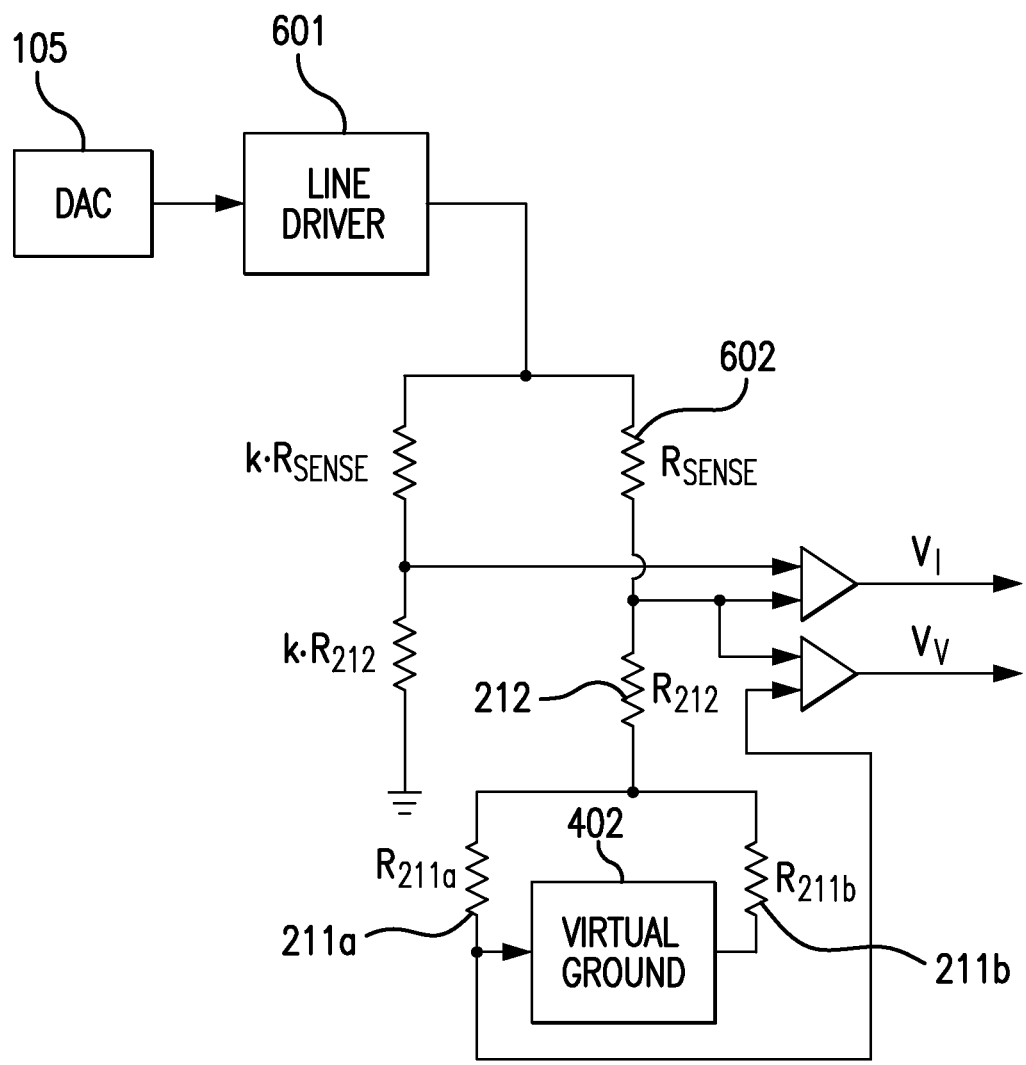
FIG. 9 depicts a schematic diagram illustrating a bridge configuration according to one embodiment.
Figure 10A:
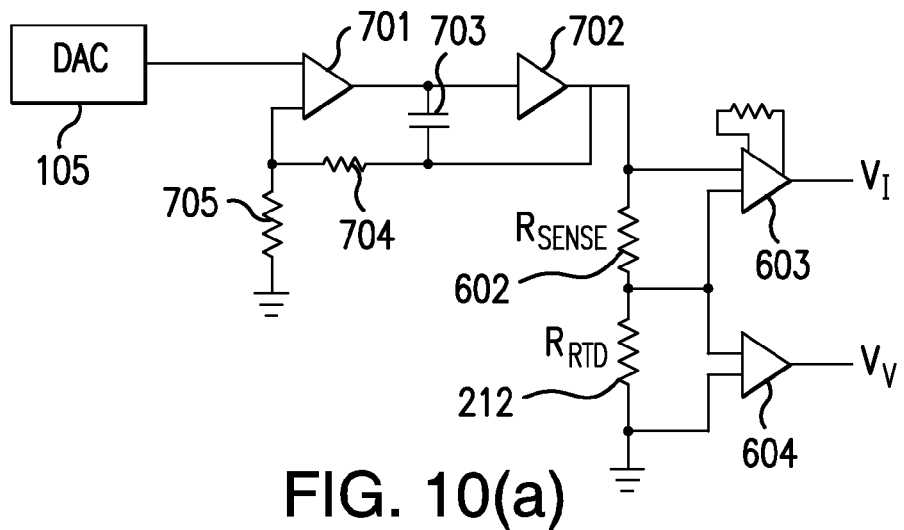
FIGS. 10A-10E depict schematic diagrams illustrating various low-pass filtering configurations that may be used in embodiments of the microfluidic system.
Figure 10B:
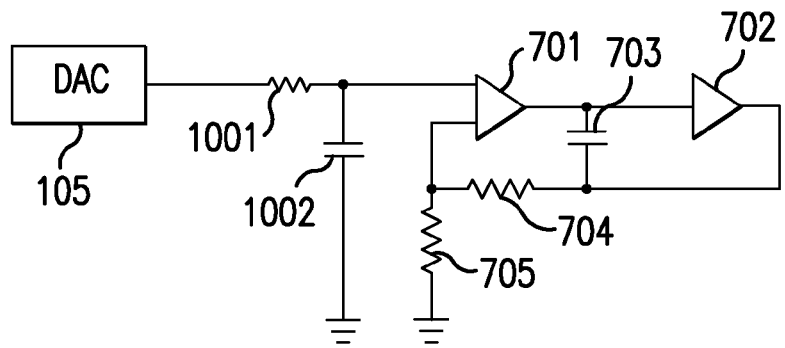
Figure 10C:
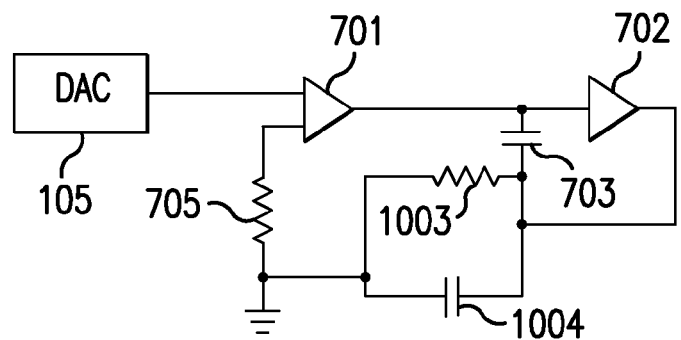
Figure 10D:
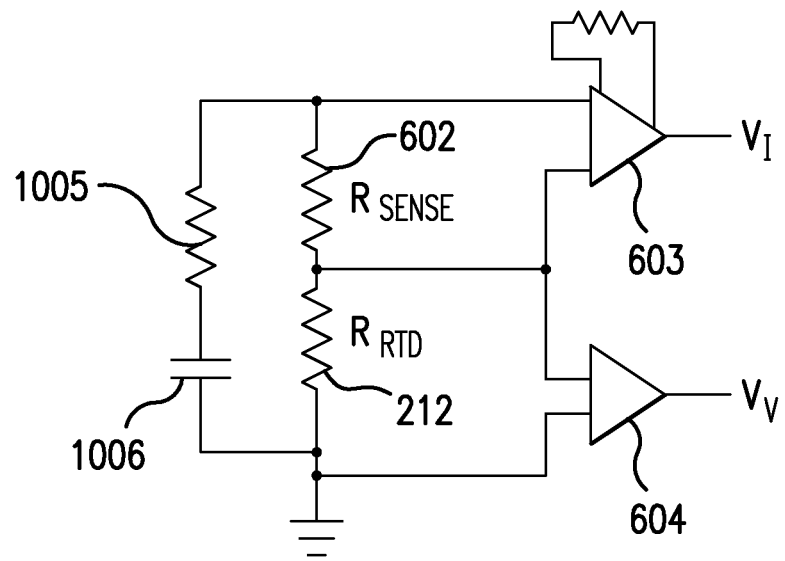
Figure 10E:
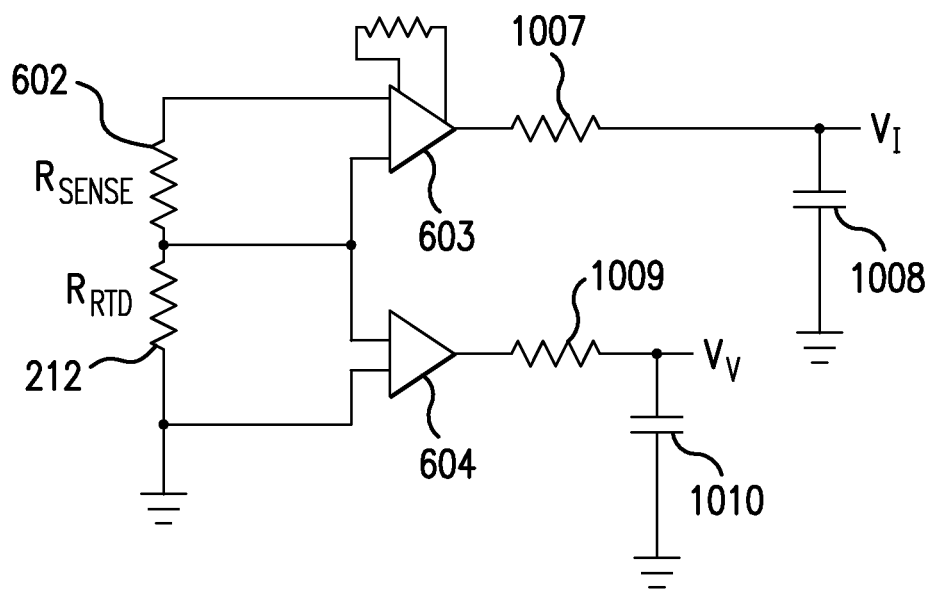

Some alternative circuit configurations may improve SNR. For example, one embodiment to improve SNR is to use a bridge configuration to remove the common mode voltage from the current sensing signal. This alternative circuit configuration is shown in FIG. 9. In this embodiment, a voltage divider with approximately the same ratio as the sense resistor 602 to the associated RTD 212 is formed. The reference voltage divider is insensitive to temperature because the scaling factor, k, is large (e.g., 100) to ensure low Joule heating. Thus, the reference voltage divider forms a stable reference voltage and improves the SNR of the current sensing signal Vcurrent (shown in FIG. 9 as $V_I$).

Further, it may be desirable to use certain low-pass filtering components to condition the heater drive signals and current and voltage measurement signals. FIG. 10(*a*) illustrates the configuration of the RTD circuit 501 shown in FIGS. 5 and 6 along with its connections with DAC 105 and RTD 212. Alternative circuit configurations utilizing low-pass filtering components are shown in FIGS. 10(*b*)-10(*e*). FIG. 10(*b*) illustrates a pre-filter power buffer configuration in which resistor 1001 and capacitor 1002 have been added between DAC 105 and line driver circuit 601. FIG. 10(*c*) illustrates a filter power buffer feedback configuration in which resistor 1003 and capacitor 1004 have been added to the configuration of line driver circuit 601. FIG. 10(*d*) illustrates a parallel low-pass filter configuration in which resistor 1005 and capacitor 1006 have been added in parallel to the sense resistor 602 and RTD 212 series. FIG. 10(*e*) illustrates a low-pass filter output configuration in which resistor 1007 and capacitor 1008 have been added at the output of differential amplifier 603 and in which resistor 1009 and capacitor 1010 have been added at the output of differential amplifier 604. In these configurations, the cut-off frequencies would be chosen to eliminate unwanted noise while preserving the ability to provide rapid closed-loop thermal control.

Another feature of some embodiments of the present invention is that the digitization of data and digital closed-loop control allow for the development of sophisticated digital algorithms. One such algorithm may be used to correct for the parasitic resistances which exist between the multiplexed RTDs 212. For instance, an electrical model may be used to solve the resistance network while accounting for the coupling caused by the parasitic resistances. Further, the system controller 103 may be configured to first measure the sheet resistance of the lead layer using the pair of common electrodes. Then, the sheet resistance of the lead layer could be used as an input into the above mentioned electrical model.

In addition, it is not necessary the driving source be based on direct current (DC). The driving source may instead be based on alternating current (AC). Thus, according to one embodiment of the present invention, the amount of heat delivered to the device may be controlled through amplitude modulation, the alternating polarity concepts described above may be used to minimize waste heat and deliver excellent temperature measurements, and the driving source may be based on AC.

It may be desirable to drive with AC rather than DC for a variety of reasons, which may include but are not limited to reducing power consumption or reducing the potential for electrolysis due to current leakage into a fluid filled microchannel 202. The electrolysis of water can be a problem in microfluidic systems as the gases that are formed can result in bubbles that block the microchannel 202 and prevent fluid flow. The use of high frequency (e.g., >1 kHz) can reduce or eliminate the formation of bubbles while allowing the high root-mean-square (RMS) potential required for the desired heating.

In some embodiments, the AC heater driving signal may be any suitable waveform. Examples include sine, square, saw-tooth, and triangle waveforms. All of the methods described above about amplitude modulation and alternating polarity are applicable to AC heater driving signals. By driving alternating channels with signals that are 180 degrees out of phase, the benefits of the alternating polarity concept are retained. The phase shift can be realized through software that drives the DACs 105 or through hardware (e.g. including inverters on some channels). One consideration in such a system is the fast response of the amplifiers used.

In another aspect, the alternating polarity concept could be used to minimize waste heat and deliver high quality temperature measurements without using the RTDs 212 as heating elements. This configuration may be desirable if one has a need to determine the temperature on the microfluidic device 101 but has some other means of heating (e.g., when the device is heated by an external means). Using the RTDs 212 as sensors only is easily realized using the techniques described above. In this configuration, a fixed driving potential may be used with no amplitude modulation. This configuration could, optionally, include the bridge configuration shown schematically in FIG. 9.

Figure 14:
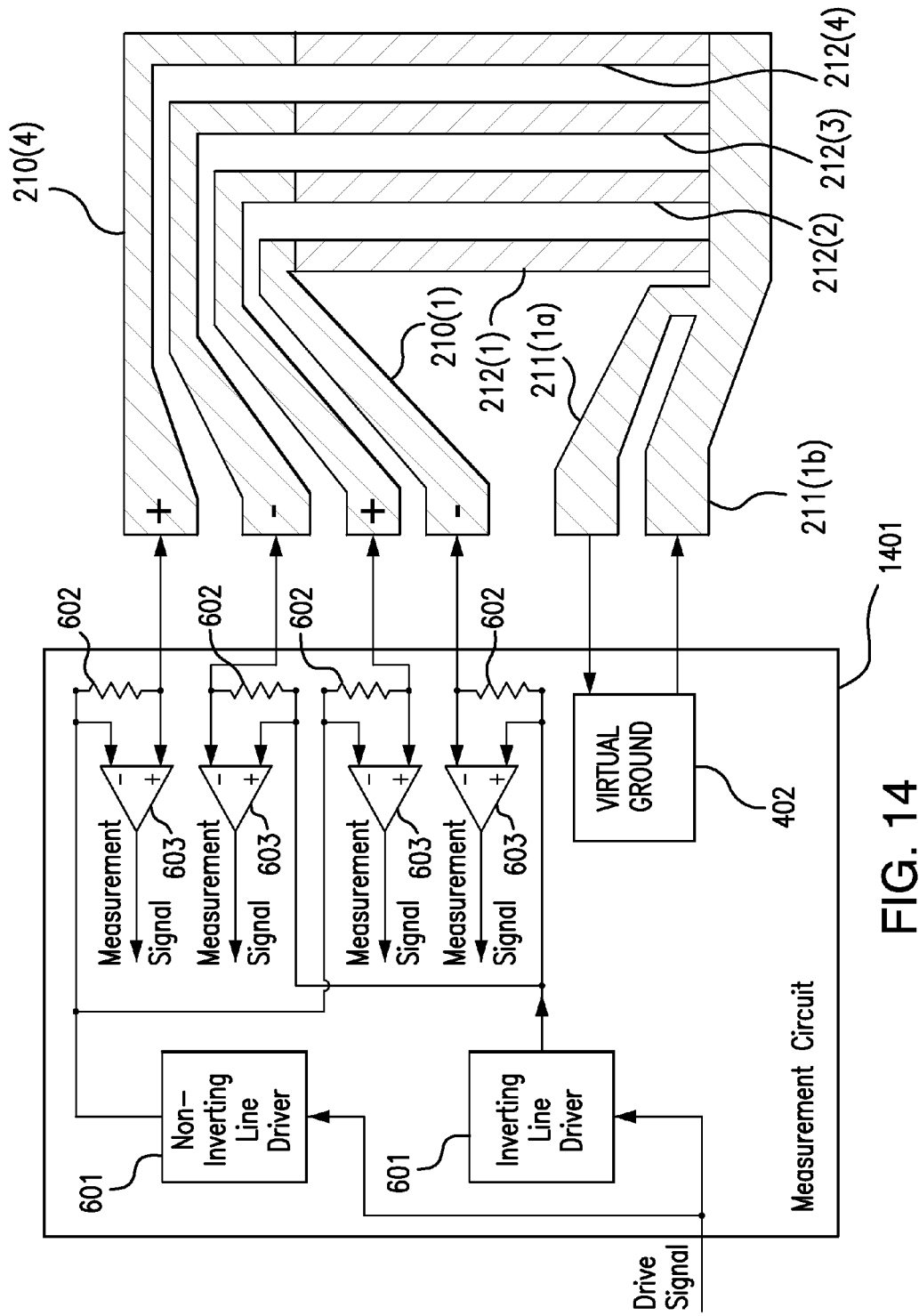
FIG. 14 depicts a block diagram illustrating alternating polarity temperature measurement of 4 sensors using a single driving signal in accordance with one embodiment.

FIG. 14 illustrates one embodiment of a configuration capable of using RTDs 212 for temperature measurement only. The temperature measurement circuit 1401 shown in FIG. 14 may receive a single drive signal used for driving all of the RTDs 212. The alternating polarity may be achieved by running the drive signal for the odd RTDs 212 (e.g., RTDs 212(1), 212(3) etc.) through an inverting line driver 601 while running the drive signal for the even RTDs 212 (e.g., RTDs 212(2), 212(4) etc.) through a non-inverting line driver 601. Measurement circuit 1401 may use a bridge configuration to form reference voltage dividers. The fixed driving potential of the driving signal is preferably small to minimize self-heating and could be generated by a multifunction DAQ device such as, for example, PXI-6289, a voltage reference IC such as, for example, MAXIM's MAX6138, or a zener diode. Moreover, only 1 measurement per channel is required to determine temperature in this system because the driving potential is fixed.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A method for individually controlling a plurality of resistive thermal detectors (RTDs) of a microfluidic device of a microfluidic system, wherein the RTDs are each adjacent to a portion of an associated one of the plurality of microchannels, the method comprising:
   generating heater control signals having alternating polarities to drive the plurality of RTDs;
   supplying the heater control signals to the plurality of RTDs so that adjacent RTDs of the plurality of RTDs are driven with heater control signals having opposite polarities relative to each other;
   minimizing current in first and second common electrodes by connecting the first and second common electrodes to a virtual ground circuit, wherein the first and second common electrodes are each connected to each RTD of the plurality of RTDs;
   sensing a temperature of each of the plurality of RTDs by using the first and second common electrodes; and
   updating the heater control signals using the sensed temperatures of the plurality of RTDs.

2. The method of claim 1, wherein the heater control signals are generated and updated based on a polymerase chain reaction (PCR) profile or on a temperature ramp profile.

3. The method of claim 1, wherein the minimizing the current in the first and second common electrodes comprises determining a current imbalance between currents of the heating control signals supplied to the plurality of RTDs.

4. The method of claim 3, wherein the minimizing the current in the first and second common electrodes further comprises sourcing/sinking the determined current imbalance.

5. The method of claim 1, further comprising preventing the heater control signals from having a voltage lower than a minimum voltage limit.

6. The method of claim 1, wherein the heater control signals are generated so that deoxyribonucleic acid (DNA) contained in the portions of the associated ones of the plurality of microchannels is amplified through a polymerase chain reaction (PCR).

7. The method of claim 1, wherein the heater control signals are generated so as to ramp the temperature of the first and second RTDs.

8. The method of claim 1, wherein the microfluidic device further comprises a second plurality of RTDs; the method further comprising:
   generating second heater control signals having alternating polarities to drive the second plurality of RTDs;
   supplying the second heater control signals to the second plurality of RTDs so that adjacent RTDs of the second plurality of RTDs are driven with second heater control signals having opposite polarities;
   minimizing current in third and fourth common electrodes, wherein the third and fourth common electrodes are each connected to each RTD of the second plurality of RTDs;
   sensing a temperature of each of the second plurality of RTDs; and
   updating the second heater control signals using the sensed temperatures of the second plurality of RTDs.

9. The method of claim 8, wherein each of the second plurality of RTDs is adjacent to a second portion of an associated one of the plurality of microchannels;
   the heater control signals that drive the plurality of RTDs are generated so that deoxyribonucleic acid (DNA) contained in the associated ones of the plurality of microchannels is amplified;
   the second heater control signals that drive the second plurality of RTDs are generated so as to ramp the temperature of the second plurality of RTDs.

10. The method of claim 9, wherein the DNA amplification is achieved through a polymerase chain reaction (PCR).

11. The method of claim 8, wherein the microfluidic device further comprises a second plurality of microchannels, each of the second plurality of RTDs being adjacent to a portion of an associated one of the second plurality of microchannels; and
   the first and second heater control signals that respectively drive the first and second plurality of RTDs are generated so that deoxyribonucleic acid (DNA) contained in the portions of the associated ones of the plurality of microchannels and the second plurality of microchannels is amplified.

12. The method of claim 11, wherein the DNA amplification is achieved through a polymerase chain reaction (PCR).

13. The method of claim 8, wherein the microfluidic device further comprises a second plurality of microchannels, each of the second plurality of RTDs being adjacent to a portion of an associated one of the second plurality of microchannels; and
   the first and second heater control signals that respectively drive the first and second plurality of RTDs are generated to ramp the temperature of the first and second plurality of RTDs.

14. The method of claim 1, wherein the heater control signals are updated by modulating the amplitude of the heater control signals.

15. The method of claim 1, wherein the heater control signals are alternating current signals.

16. The method of claim 15, wherein the heater control signals have opposite polarities when they are 180 degrees out of phase with each other.

* * * * *